United States Patent
Jaroch (10) Patent No.: US 10,808,280 B2
(45) Date of Patent: Oct. 20, 2020

(54) COMPUTATIONAL PHYLOGENETIC ANALYSIS

(71) Applicant: Colossio, Inc., Chicago, IL (US)

(72) Inventor: Joseph A. Jaroch, Chicago, IL (US)

(73) Assignee: Colossio, Inc., Chicago, IL (US)

( * ) Notice: Subject to any disclaimer, the term of this patent is extended or adjusted under 35 U.S.C. 154(b) by 437 days.

(21) Appl. No.: 15/704,157

(22) Filed: Sep. 14, 2017

(65) Prior Publication Data

US 2019/0078156 A1  Mar. 14, 2019

(51) Int. Cl.
| | | |
|---|---|---|
| *G01N 33/48* | (2006.01) | |
| *G01N 33/50* | (2006.01) | |
| *C12Q 1/6869* | (2018.01) | |
| *G16B 10/00* | (2019.01) | |
| *G16B 20/00* | (2019.01) | |
| *G16B 30/00* | (2019.01) | |
| *G16B 40/00* | (2019.01) | |
| *G16B 45/00* | (2019.01) | |

(52) U.S. Cl.
CPC ........... *C12Q 1/6869* (2013.01); *G16B 10/00* (2019.02); *G16B 20/00* (2019.02); *G16B 30/00* (2019.02); *G16B 40/00* (2019.02); *G16B 45/00* (2019.02)

(58) Field of Classification Search
None
See application file for complete search history.

(56) References Cited

U.S. PATENT DOCUMENTS

2015/0280907 A1* 10/2015 Kocher ................. G06F 21/602
380/30

FOREIGN PATENT DOCUMENTS

WO    WO-2016130557 A1 *  8/2016  ........... H04L 9/0869

OTHER PUBLICATIONS

Belinski ES. Approximation of functions of several variables by trigonometric polynomials woth given number of harmonics, and estimates of e-entropy. Analysis Mathematica, vol. 15, pp. 67-74. (Year: 1989).*

* cited by examiner

*Primary Examiner* — Russell S Negin
(74) *Attorney, Agent, or Firm* — Barnes & Thornburg LLP (57) ABSTRACT

Systems and a method for computationally analyzing genetic base pairs are provided. In one or more aspects, a system includes a memory and a processor coupled to the memory. The processor is configured to receive a number of genetic sequences from a genetic sequencer device. The processor can generate, for each genetic sequence, a binary sequence. Each binary sequence is partitioned into a set of binary strings. Each binary string includes multiple binary base pairs. A set of entropy values are determined, each entropy value is associated with a binary string, and an entropy distribution function (EDF) is generated based on the set of entropy values.

17 Claims, 9 Drawing Sheets

Specification includes a Sequence Listing.

COMPUTATIONAL PHYLOGENETIC ANALYSIS

TECHNICAL FIELD

The present disclosure generally relates to genetic analysis and more specifically relates to computational phylogenetic analysis.

BACKGROUND

Deoxyribonucleic acid (DNA) is the building block of life and is present in nearly every living organism as the main constituent of chromosomes. Recent advancements in genetic sequencing have opened the door to a deeper understanding of how mutations occur and how living organisms function. As could be expected, the number of possible permutations in a genome is vast, which produces challenges for identifying specific changes or the purpose of particular genes. A fundamental aspect of genetic research is based on modeling and determining the progression of gene mutations in order to track the origin of a change in the gene, for example, in the gene base pairs. This is particularly relevant in researching viruses as small mutations can result in significantly different profile and may require different strategies for mitigation.

A base pair is a unit building block of the DNA double helix consisting of two nucleobases bound to each other by hydrogen bonds. The size of an individual gene or an organism's entire genome can be measured in base pairs because DNA is usually double-stranded. The base pairs are adenine-thymine (A-T) and guanine-cytosine (G-C) in DNA, and adenine-uracil (A-U) and G-C in ribonucleic acid (RNA) or in hybrid DNA-RNA pairing.

Currently, the processes for analyzing viruses and tracking their gene sequence changes are heavily dependent upon manual research, annotating the genetic sequence and using string comparison algorithms to determine what base pairs have changed between mutations. This is labor and computationally intensive, and can cause delays in identifying a particular virus, which can have significant implications to public health.

SUMMARY

The disclosed system and methods are provided for performing a computational phylogenetic analysis. The disclosed solution can operate to analyze the arbitrary, unannotated base pairs comprising a particular genetic sequence, to efficiently categorize the base pairs and compare the genome to a number of other genomes to identify mutations. The subject technology can use computational phylogenetic analysis leveraging concepts of machine learning. The subject solution can automate the process of identifying mutations through computationally analyzing the base pairs of a virus, a bacterium, or a complete organism.

According to certain aspects of the present disclosure, a system for computationally analyzing genetic base pairs includes a memory and a processor coupled to the memory. The processor may receive a number of genetic sequences from a genetic sequencer device. The processor can generate, for each genetic sequence, a binary sequence. Each binary sequence is partitioned into a set of binary strings. Each binary string may include multiple binary base pairs. A set of entropy values can be determined, each entropy value of which is associated with a binary string, and an entropy distribution function (EDF) may be generated based on the set of entropy values.

According to certain aspects of the present disclosure, a method of computationally analyzing genetic base pairs includes configuring a processor to receive a number of genetic sequences from a genetic sequencer device, and to generate, for each genetic sequence, a binary sequence. The method further includes configuring a genetic sequence analyzer to partition the binary sequence into multiple binary strings. Each binary string includes a number of binary base pairs. The genetic sequence analyzer can further generate a polynomial EDF based on entropy values determined for the binary strings.

According to certain aspects of the present disclosure, a system may include a genetic sequencer device to generate multiple genetic sequences associated with multiple genetic samples. The system further includes a processor and a genetic sequence analyzer. The processor can be configured to generate, for each genetic sequence, a binary sequence. The genetic sequence analyzer can analyze the multiple genetic sequences by partitioning each binary sequence into multiple binary strings. Each binary string may include a number of binary base pairs. The genetic sequence analyzer can further generate an EDF based on entropy values determined for the binary strings.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

General Overview

This subject technology provides a method and a system for analyzing the arbitrary, unannotated base pairs including a particular genetic sequence, and efficiently categorizing and comparing the genome to a number of other genomes to identify mutations. The analysis can be performed as a phylogenetic analysis based, for example, on concepts of machine learning. The subject solution has been designed to automate the process of identifying mutations by computationally analyzing the base pairs, for example, of a virus, a bacterium, or a complete organism. The base pairs may be adenine-thymine (A-T) and guanine-cytosine (G-C) in DNA, and adenine-uracil (A-U) and G-C in ribonucleic acid (RNA) or in hybrid DNA-RNA pairing. According to an aspect of the present disclosure, there is provided a method for identifying the progression of mutations by creating a binary representation of the DNA base pairs, partitioning the base pairs into groups such as strings, and calculating the entropy of these strings as a polynomial function of a high order (e.g., 10 or more). The entropy sequence may then be associating and aligning to multiple other entropy sequences from other samples to identify areas (sections) of the entropy sequences that overlap and the areas that differ.

According to another aspect of the subject technology, there is provided a method for ranking and determining the proximity between variants of each genetic sequence, and supplying output to indicate sequences with the lowest deviation. According to yet another aspect, of the present invention, there is provided a method for determining the number of mutations between sequences, and identifying areas of each sequence that are more susceptible to producing stable changes.

Example System Architecture

Figure 1:
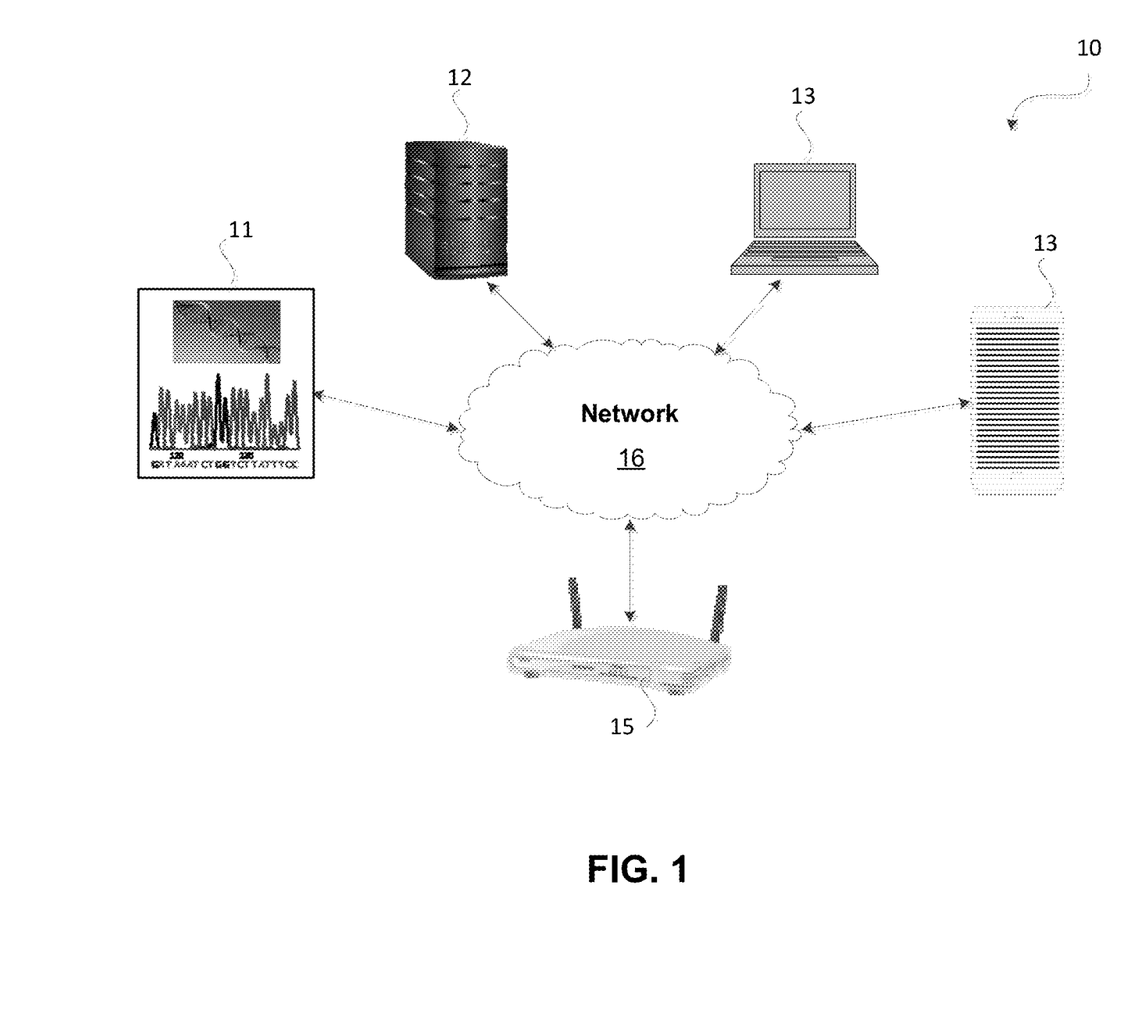
FIG. 1 illustrates an example environment in which the subject technology is implemented.

FIG. 1 illustrates an example environment in which the subject technology is implemented. The architecture 10 includes one or more devices 11, a server 12, a computing device 13, a portable communication device 14 and an access point 15 communicating (e.g., wirelessly) over a network 16. The one or more devices 11 include a genetic sequencer such as a deoxyribonucleic acid (DNA) sequencer. The DNA sequencer is a machine that can automate the process of DNA sequencing. The DNA sequencer is used to determine the order of the four genetic bases including G (guanine), C (cytosine), A (adenine) and T (thymine) bases in a genetic sample. The output of the DNA sequencer can be a text string, known as a read.

In some implementations, the server 12 is a local server or a cloud server capable of cloud computing. The computing device 13 may be a personal computer such as a laptop computer, and the portable communication device 14 may be a smart phone or a personal digital assistant (PDA). The access point 15 may be a wireless access point that facilitates communication, via the network 16, of the device(s) 11, the server 12, the computing device 13 and the portable communication device 14.

Examples of the network 16 include any one or more of a personal area network (PAN), a local area network (LAN), a campus area network (CAN), a metropolitan area network (MAN), a wide area network (WAN), a virtual private network (VPN), a broadband network (BBN), the Internet and the like. Further, the network 16 can include, but is not limited to, any one or more of the following network topologies, including a bus network, a star network, a ring network, a mesh network, a star-bus network, a tree or hierarchical network and the like.

In some implementations, the server 12 can receive a number of genetic sequences (e.g., DNA sequences) from the genetic sequencer (e.g., device(s) 11) for processing. In one or more implementations, any of the computing device 13 and/or the portable communication device 14 may receive the genetic sequences from the genetic sequencer device. For example, the computing device 13 and/or the portable communication device 14 may have capabilities, such as processing power and one or more suitable applications to perform processing of the received genetic sequences as described herein. In some embodiments, the genetic sequencer functionalities may be implemented in one or more of the server 12, the computing device 13 and/or the portable communication device 14.

Figure 2:
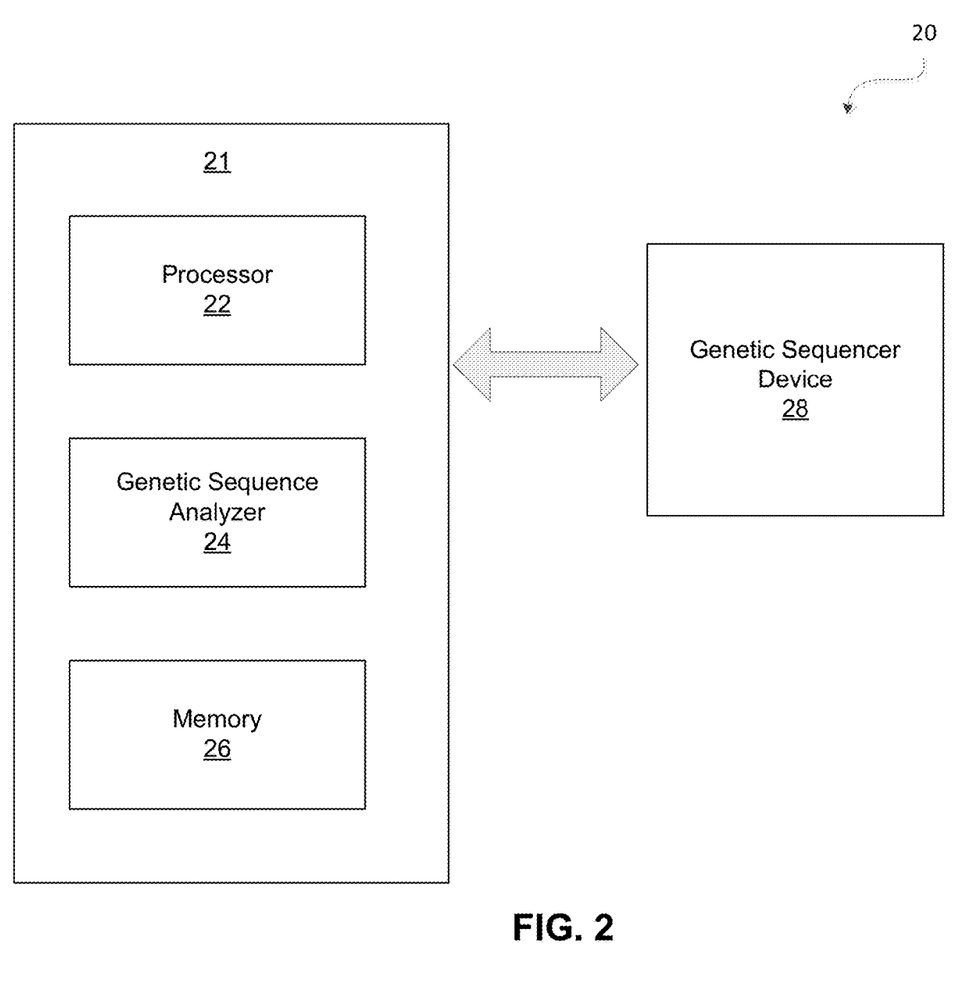
FIG. 2 is a block diagram illustrating an example architecture of a system for computationally analyzing genetic base pairs, according to certain aspects of the disclosure.

FIG. 2 is a block diagram illustrating an example architecture of a system 20 for computationally analyzing genetic base pairs, according to certain aspects of the disclosure. The system 20 includes a server 21 and a genetic sequencer device 28. The server 21 includes a processor 22, a genetic sequence analyzer 24 and a memory 26. Examples of the server 21 can be any of the server 12, the computing device 13 and/or the portable communication device 14 of FIG. 1 with a substantial processing power. In some aspects, the processor 22 includes a number of processor cores, for example, more than eight processor cores to allow parallel processing. The genetic sequence analyzer 24 may be implemented in hardware, software, and/or firmware or may be a part of the processor 22. In some embodiments, the memory 26 can be, but is not limited to, a random access memory (RAM), for example, with at least 16 gigabytes storage capacity. In some implementations, the functionalities of the genetic sequencer device 28 may be integrated with the server 21.

In one or more implementations, the processor 22 receives a number of genetic sequences from a genetic sequencer device 28 and generates a binary sequence for each genetic sequence. The binary sequence is a binary representation (e.g., G=00, T=01, A=10, C=11) of the DNA base pairs (e.g., A-T and G-C). The genetic sequence analyzer 24 may partition each binary sequence (e.g., associated with a DNA sample) into a set of binary strings (e.g., binary groups or chunks). Each binary string may include multiple binary base pairs. The genetic sequence analyzer 24 may determine a set of entropy (e.g., Shannon entropy) values associated with the binary strings and generate an entropy distribution function (EDF) based on the set of entropy values. In some embodiments, the EDF is a substantially high order polynomial function.

The exponents of terms of the polynomial function can be determined based on the set of entropy values, and the coefficients of the terms of the polynomial function may be determined based on an average count of the multiple binary base pairs. For example, if there are three binary strings and the set of entropy values is [4, 5, 11], the resultant EDF can have 4, 5, and 11 as the exponents of terms of the polynomial (e.g., $x^4$, $x^5$ and $x^{11}$). Depending on the use-case and the tuning of the algorithm, the coefficients of the polynomial terms can be set to the average of the base pairs in the binary string. For example, if the first binary string is 10 base pairs long and the total of the base pairs when translated into their binary representation equals 30, the coefficient associated with the first binary string (e.g., coefficient of the term $x^4$) can be 3 (e.g., =30/10). And if the second and third binary strings are 15 and 5 base pairs long (e.g., out of total of 30 base pairs=10+15+5) the polynomial can be expressed as: $3x^4+2x^5+6x^{11}$, where the coefficients values 2 and 6 are determined by the ratios 30/15 and 30/5, respectively. This ensures that not only the entropy values but also the content of a given binary string is taken into account when formulating the complete EDF polynomial. In some implementations, the partitioning of the binary sequences of different genetic (e.g., DNA) sample, calculating corresponding entropy values and EDFs can be performed by the processor 22.

The same procedure discussed above with respect to a generic sequence can be applied to other genetic sequences. In other words, for each genetic sample, the subject technology attains a set of entropy values and a corresponding EDF (e.g., a polynomial function).

The processor 22 or the genetic sequence analyzer 24 can further analyze the attained EDFs for different genetic samples and identify one or more local maxima (and/or minima) in some of the attained EDFs. In one or more implementations, the processor 22 or the genetic sequence analyzer 24 may compare the EDF of the first genetic sample with EDFs corresponding to multiple genetic samples and identify substantially overlapping areas (sections) in two or more EDFs associated with different DNA samples, as discussed in more detail herein.

Figure 3:
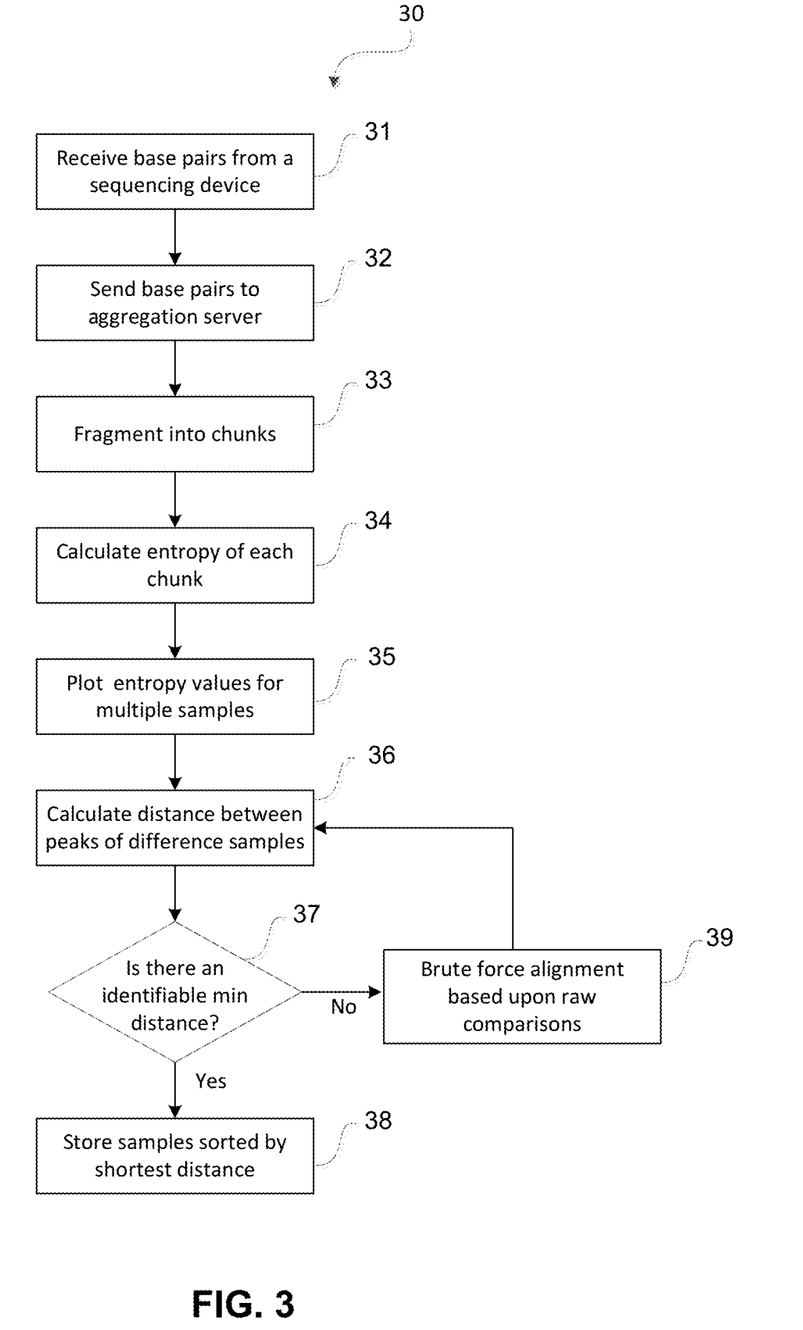
FIG. 3 is a flow diagram illustrating an example process for computationally analyzing genetic base pairs, according to certain aspects of the disclosure.

FIG. 3 is a flow diagram illustrating an example process 30 for computationally analyzing genetic base pairs, according to certain aspects of the disclosure. The process 30 may be implemented by, but not limited to, any of the processor 22 or the genetic sequence analyzer 24 of FIG. 2. The process 30 begins with an operation block 31, where a number of genetic sequences (e.g., DNA sequences) including genetic base pairs are received from a sequencer device (e.g., 11 of FIG. 1 or 28 of FIG. 2). At an operation block 32, the genetic sequences including the genetic base pairs are sent to an aggregation server (e.g., 12 of FIG. 1 or 21 of FIG. 2). The genetic sequences are converted to binary format and each genetic sequence is partitioned into a number of binary strings (e.g., chunks).

In some implementations, the genetic sequences may be fragmented into equal-sized partitions. The number of binary strings can vary depending on configuration but generally a binary string may be no greater than 100 base pairs in length to ensure an optimum comparison. The configuration may be one of coarse configuration options presented to a user that can be tuned depending on the particular type of genetic material being analyzed. For example, filoviridae tend to be relatively small (e.g., in bytes, about 20 kilobytes), whereas full organism genomes can be many hundreds of megabytes in size. When the disclosed system is being used for organisms instead of Filoviridae, the configuration will tend to be different, based on user inputs. The partitioning may not be on any particular boundary and can be effectively random, but it allows binary strings to still be compared. It should be noted that the precise per-expressed-gene splitting done manually by some researchers may not be required for the disclosed process to be effective.

In order to better understand the concept of partitioning of the generic sequences into binary strings (chunks), an example binary string of genetic bases, for instance, of 100 genetic bases such as SEQ ID NO: 1:

"GTACATAGATGATAGATATAGATACGATAGCCAGATGACG

TGATAGATAAGCATGCTAGTAGTGCAGATAGATAATGAAT

ACTAGACTTGGAACTAGATC"

is considered for analysis herein. For simplicity, the binary pairs 00, 01, 10 and 11 of the example binary string are represented by their respective symbols G, T, A and C. For the initial identification of a delimiter between binary strings, using a brute force technique, a search can be performed to identify the longest string which repeats the highest number of times in the example binary string. An initial search window size can be chosen to be, for example, smaller of 10 or equal to one fifth of the original base string size (e.g., 100). With an initial search window size of 10, each set of 10 characters is iterated through in the binary string and the count of occurrences later in the string is identified. For instance, if the characters at position [2-11] are found at positions [30-39] and nowhere else, the algorithm would indicate a total of one match, of ten characters in total.

In some implementations, the size of the search window is reduced by one to nine and the process is repeated. The process may continue until the size of the search window reaches four and can terminate at that point, as below four characters, the likelihood of there being a random occurrence can be too high to be acceptable. In the example binary string, the identified delimiter is [GATAGATA], which appears three times and is eight characters long, resulting in a score (e.g., occurrence×length) of 16. In calculating the score of 16 (2×8), the first occurrence (of 3) is not included in calculating the score 16 as it will always be present. The example binary string with the identified delimiter highlighted is shown below within SEQ ID NO: 2:

"GTACATAGATGATAGATATAGATACGATAGCCAGATGACGTGATAGATA
AGCATGCTAGTAGTGCAGATAGATAATGAATACTAGACTTGGAACTAGAT
C"

The binary string is then split into four binary sequences with the delimiters removed and the entropy calculation takes place on each binary sequence.

Now returning to the process 30, at operation block 34, for each binary sequence an entropy value (e.g., Shannon entropy) is calculated. Entropy values for each genetic sample are used to generate an EDF (e.g., a polynomial), as discussed above. The polynomial for each sample is plotted and analyzed to identify local maxima (or minima) such as peaks (or valleys). At operation block 36, distance between local maxima (or minima) associated with different genetic samples are calculated. At control operation block 37, it is checked whether a shortest (minimum) distance between the calculated peaks is identifiable. When there is an identifiable lowest distance, at operation block 38, the binary sequences associated with different genetic samples are sorted by the shortest distance. Otherwise, when there is not an identifiable lowest distance, at operation block 39, a brute force alignment is performed based upon raw comparisons and the control is passed to operation block 36.

Figure 4:
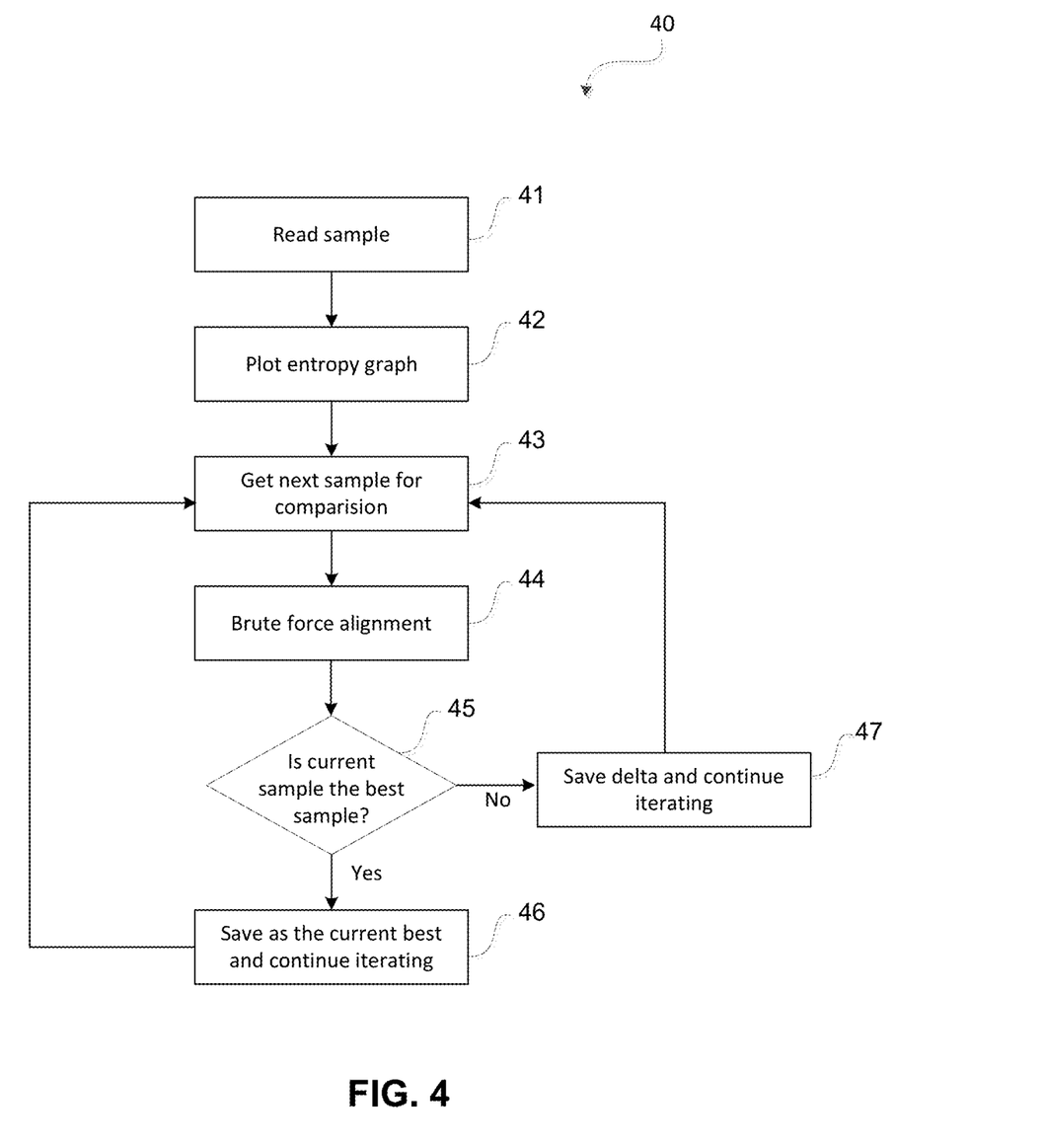
FIG. 4 is a diagram illustrating an example process for computationally analyzing genetic base pairs, in which the subject technology is implemented.

FIG. 4 is a diagram illustrating an example process 40 for computationally analyzing genetic base pairs, in which the subject technology is implemented. The process 40 may be implemented by, but is not limited to, any of the processor 22 or the genetic sequence analyzer 24 of FIG. 2. The process 40 begins with an operation block 41, where a number of genetic sequences (e.g., DNA sequences) including genetic base pairs are received from a sequencer device (e.g., 11 of FIG. 1 or 28 of FIG. 2), converted to binary format, partitioned, and for which entropy values are calculated as discussed above. At an operation block 42, the EDF polynomials associated with different genetic samples are plotted. At operation block 43, the next genetic sample (e.g., the second genetic sample) for comparison with the genetic first sample is selected. A brute force alignment of the EDF polynomials of the selected genetic sample and the first genetic sample is performed at operation block 44. At control operation block 45, it is determined whether the current selected genetic sample the best genetic sample, the peak of polynomial in at least some overlapping section has the lowest difference with a respective peak in the polynomial of the first genetic sample. When the answer is yes, at operation block 46, the current selected sample is saved (e.g., in memory 26 of FIG. 2) and the control is passed to the operation block 43 for continuation of the iterations in order to find the best genetic sample. Otherwise, when the answer is no, at operation block 47, the current difference (e.g., delta) between corresponding peaks is saved (e.g., in memory 26 of FIG. 2) and the control is passed to the operation block 43 for continuation of the iterations.

Figure 5:
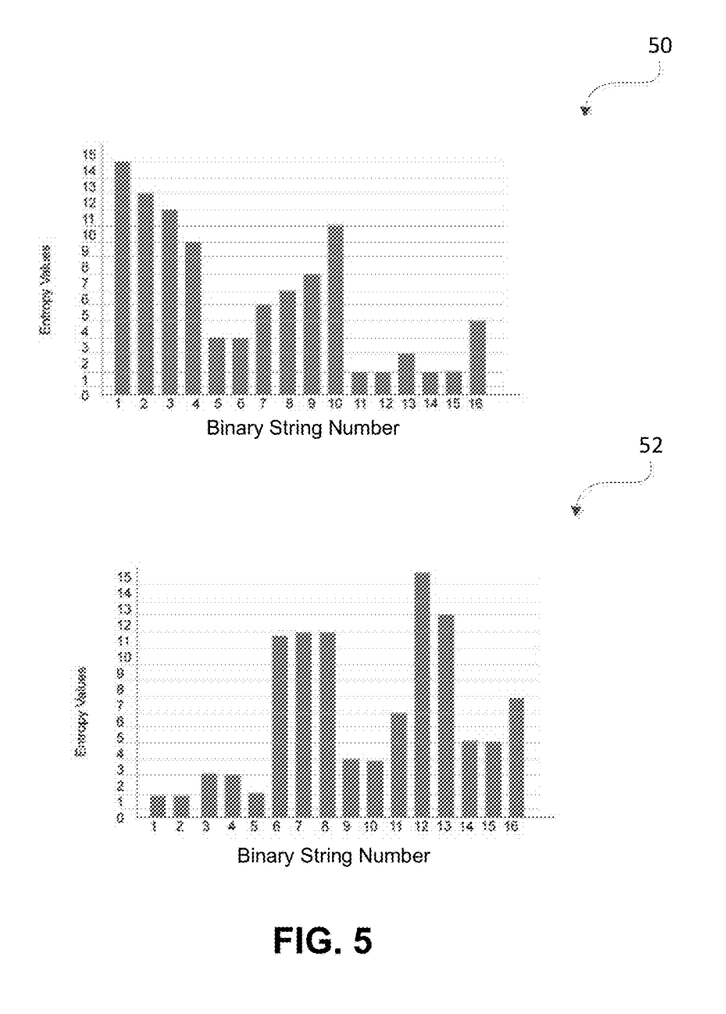
FIG. 5 illustrates charts of example entropy values for a number of binary strings of two partitioned genetic sequences, according to certain aspects of the disclosure.

FIG. 5 illustrates charts 50 and 52 of example entropy values for a number of binary strings of two partitioned genetic sequences, according to certain aspects of the disclosure. The charts 50 and 52 show calculated entropy values for a first and a second genetic sample, respectively. The entropy values in the charts 50 and 52 are plotted versus a binary string numbers from 1 to 16. In other words, each of the genetic sequences associated with the first and the second genetic samples were partitioned into 16 binary strings numbered from 1 to 16. The chart 50 shows peaks at binary string number 1, 10 and 16. The chart 52 has 4 identifiable peaks at binary string number 3, 7, 12 and 16.

Figure 6:
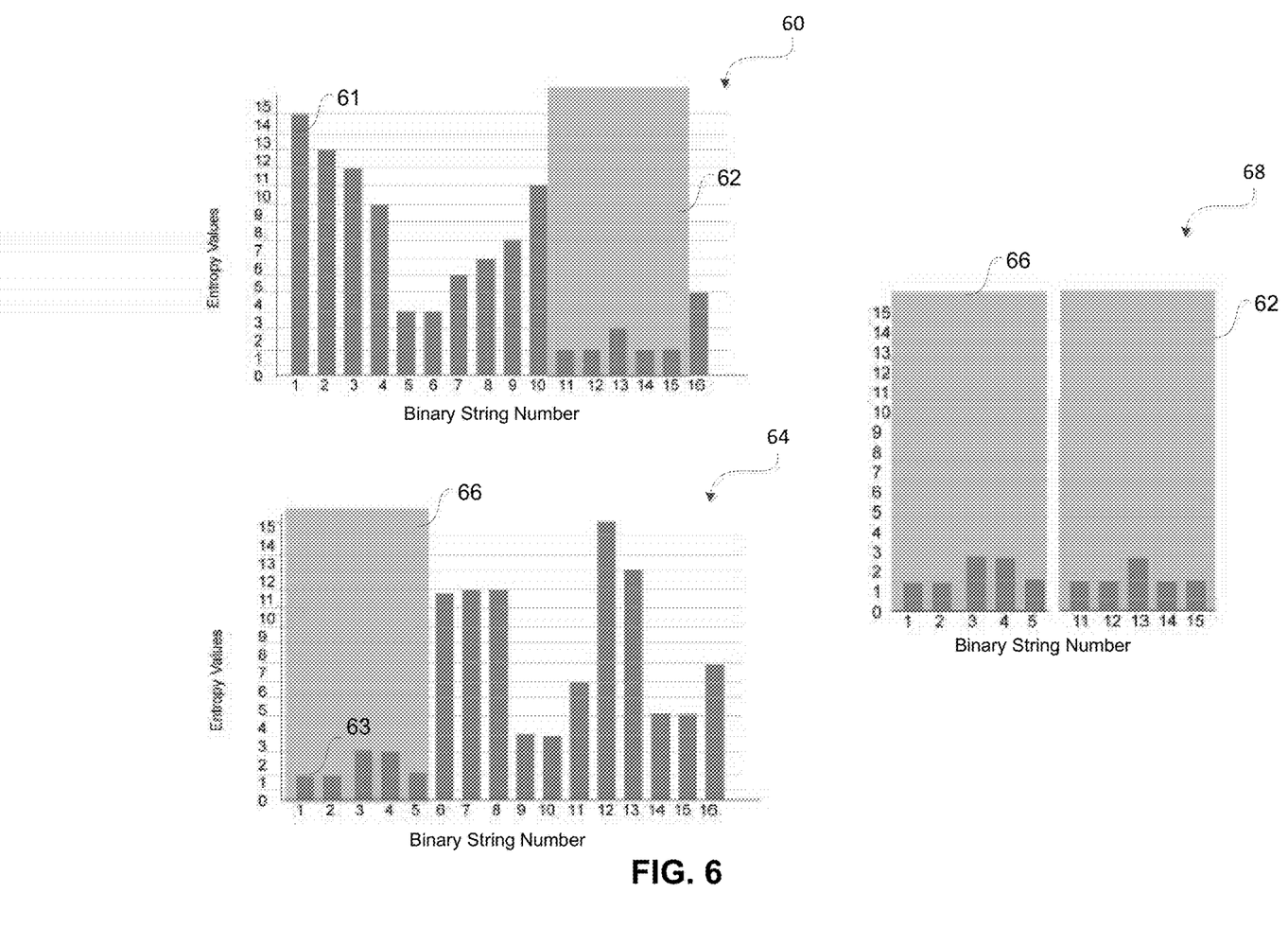
FIG. 6 illustrates charts of example entropy values for a number of binary strings of two partitioned genetic sequences and example search windows, according to certain aspects of the disclosure.

FIG. 6 illustrates charts 60, 64 and 68 of example entropy values for a number of binary strings of two partitioned genetic sequences and example search windows, according to certain aspects of the disclosure. The charts 60 and 64 depict the same entropy distribution functions as shown in the charts 50 and 52 of FIG. 5, respectively. In the chart 60, a search window (e.g., variable-width search window) 62 is shown to include a portion of the chart 60 including binary string numbers 11 to 15 of the first genetic sample. In the chart 64, a similar window (e.g., variable-width search window) 66 is shown to include a portion of the chart 64 including binary string numbers 1 to 5 of the second genetic sample. When looking for difference between corresponding binary strings of the genetic sequences of different samples (e.g., the first and the second sample) the subject solution may use a comparison algorithm, which may be executed by the processor 22 of FIG. 2 or can be implemented by a firmware, for example, based on machine learning.

The comparison algorithm may start by comparing the entire binary strings of different samples together, for instance, by looking at the difference between entropy values of corresponding binary strings. For example, the binary string number 1 of the first genetic sample (e.g., shown in the chart 60) can be compared to the binary string number 1 of the second genetic sample (e.g., shown in the chart 64), the binary string number 2 of the first genetic sample to the binary string number 2 of the second genetic sample, and so on. The first iteration may see the ordinal positions aligned but this will change on subsequent iterations.

The comparison algorithm then may calculate the absolute value of the difference between each entropy value reading. For example, for a reading 61 associated with the binary string number 1 of the first genetic sample and a reading 63 associated with the binary string number 1 of the second genetic sample, a difference value of 13 is observed. The rest of the difference values for other respective binary string numbers of the two genetic samples read as 11, 9, 7, 2, 8, 6, etc.

The above described path can be performed across the entire binary strings of all of the genetic samples (e.g., hundreds/thousands of genetic samples). After this full-sample pass has completed, subsequent passes are performed. The subsequent passes can start by reducing the size of the comparison. For example, rather than comparing the entire binary strings (e.g., 1-16), the comparison may be made in a variable-width search window such as [1-15] and then [2-16], that is by reducing the comparison size by one and shifting once to compare.

This comparison process can be repeated, for example, by comparing search windows [1-14], [2-15], [3-16] . . . [1-13], [2-14], [3-15], [4-16] . . . , [1-12], [2-13], [3-14], [4-15], [5-16] . . . etc.

Eventually, each combination of binary strings is compared, and the relative distance between them is calculated. The intent is to find the shortest distance between samples across all of the genetic samples to identify which genetic samples are most closely related. As the width of the search window shrinks, it is more likely that groups will match but samples with both the largest and closest matches can be identified as the overall closest match.

Now returning to FIG. 6, the charts 60 and 64 can be interpreted as snapshots during the above process that a search window 62 (e.g., [11-15]) in the first sample (e.g., in chart 60 or 68) is being compared to a search window 66 (e.g., [1-5]) in the second sample (e.g., in chart 64 or chart 68). The entropy values in these two search windows do not appear to be an exact match but are close. The difference between entropy values in the two search windows are [0, 0, 0, 1, 0], resulting in a total difference of 1 for the two search windows.

Figure 7:
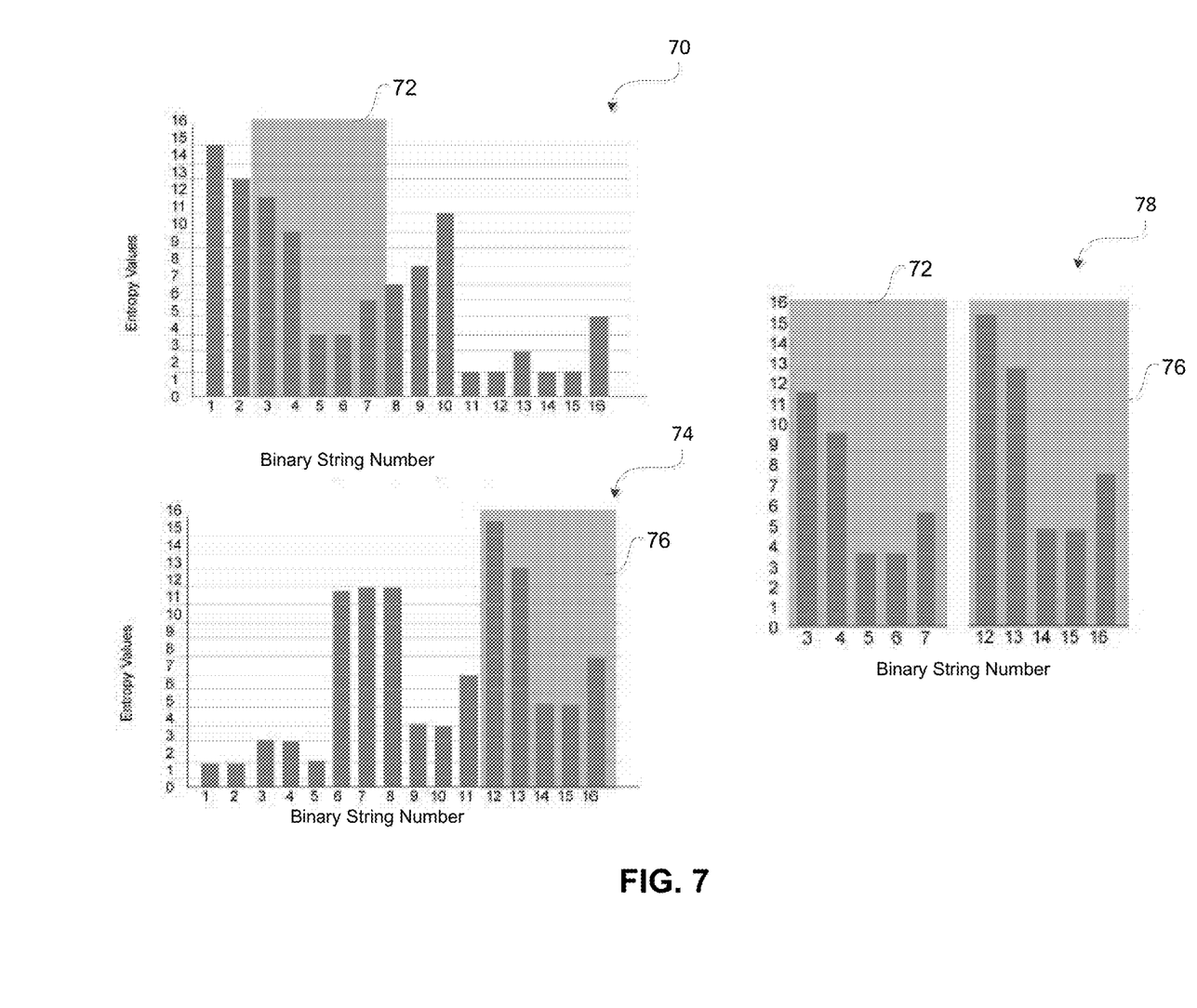
FIG. 7 illustrates charts of example entropy values for a number of binary strings of two partitioned genetic sequences and example search windows, according to certain aspects of the disclosure.

FIG. 7 illustrates charts 70, 74 and 78 of example entropy values for a number of binary strings of two partitioned genetic sequences and example search windows, according to certain aspects of the disclosure. The charts 70 and 74 depict the same entropy distribution functions as shown in the charts 50 and 52 of FIG. 5, respectively. The charts 70 and 74 can be interpreted as snapshots during the above-described comparison process that a search window 72 (e.g., [3-7]) in the first sample (e.g., in chart 70 or 78) is being compared to a search window 76 (e.g., [12-16]) in the second sample (e.g., in chart 74 or chart 78). Although the entropy values in these two search windows do not appear to be an exact match, they are quite close. The difference between entropy values are [4, 3, 1, 1, 2] resulting in a total difference of 10. Most regions may not match but, as an example of regions that don't match as closely, the search window [6-10] in the first genetic sample (e.g., chart 70) and the search window [3-7] in the second genetic sample (e.g., chart 74) produce a difference of [1, 3, 5, 4, 3], giving a total difference of 16. The comparison process can continue for the first and the second genetic samples to produce a final output score which can indicate how close these two genetic samples are. Similar comparisons can be run between the first and a third genetic sample and the first and a fourth genetic sample and so on. The overall difference values may be ranked to find the genetic samples that are the closest to one another. Identifying the distances even if the match between genetic samples may not be perfect allows the genetic samples to be clustered by proximity and the identification of generations of the genetic samples based on groups of mutations that are shared by a given sample group.

In some embodiments, the subject technology may be able to identify areas of each genetic sequence that are more susceptible to producing stable changes. For example, when two closely-matching genetic samples are identified, the differences between them can be isolated by removing the portions of the genomes that contributed to the positive match, leaving only the areas which substantially differ between the genetic samples. As more and more genetic samples are compared, it may become apparent that certain portions of a given genome are more susceptible to producing stable changes (e.g. ones that positively influence, rather than reduce, the likelihood of an "offspring" of the organism surviving). This elimination process occurs by identifying the regions of genomes which are consistent across a plurality of different samples and highlighting the regions which consistently differ. This output can be provided to the researcher to allow them to focus their investigative efforts on a more narrowly defined cross-section of the overall genome. Depending on the nature of the genome in question, it may become clear that, through the use of this technology's exclusion procedure, some regions of the genome can be consistently ignored, improving the efficiency of the research process.

Figure 8:
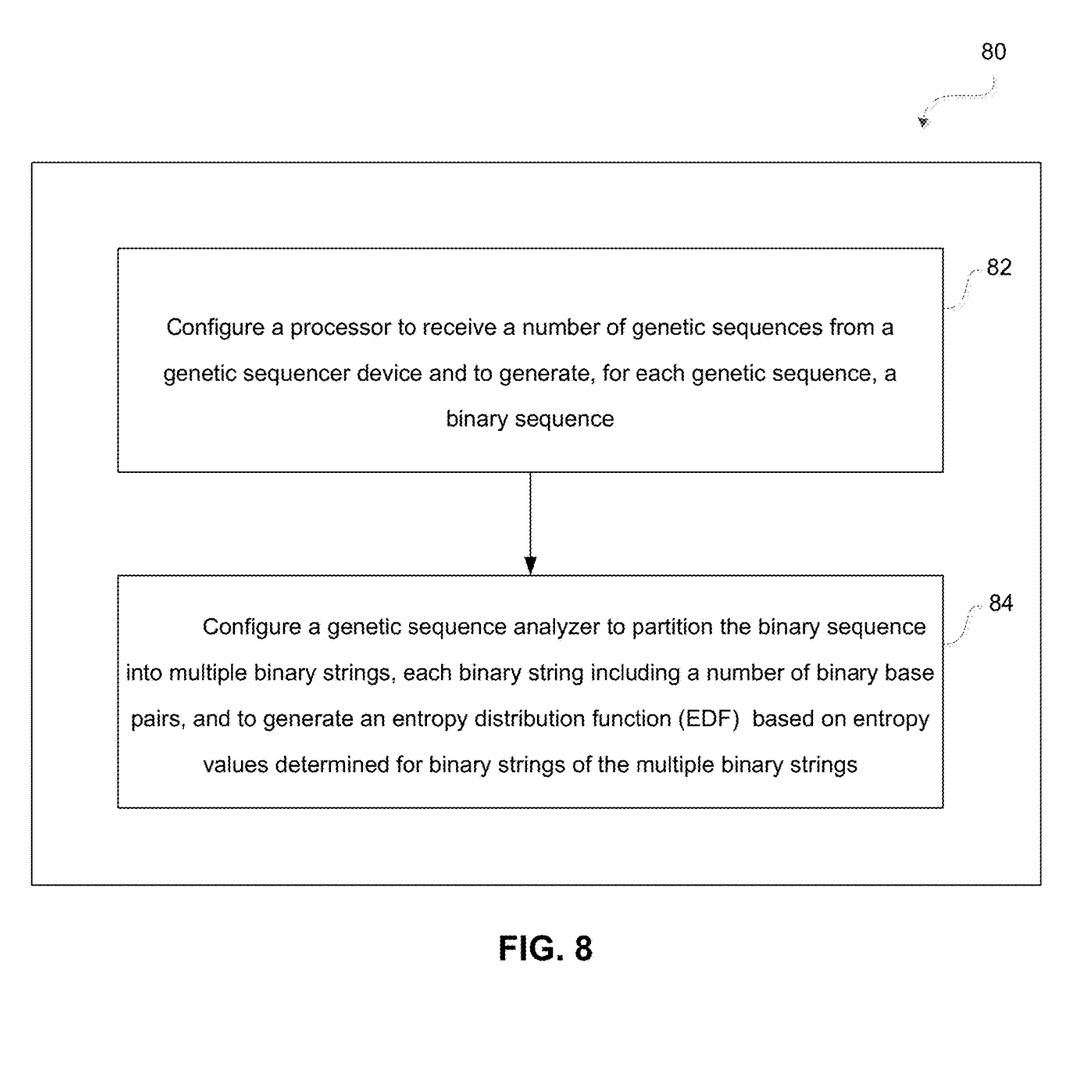
FIG. 8 is a flow diagram illustrating an example method of computationally analyzing genetic base pairs, according to certain aspects of the disclosure.

FIG. 8 is a flow diagram illustrating an example method 80 of computationally analyzing genetic base pairs, according to certain aspects of the disclosure. The method 80 includes configuring a processor (e.g., 22 of FIG. 2) to receive a number of genetic sequences from a genetic sequencer device (e.g., 11 of FIG. 1 or 28 of FIG. 2), and to generate, for each genetic sequence, a binary sequence (82). The method further includes configuring a genetic sequence analyzer (e.g., 24 of FIG. 2) to partition the binary sequence into multiple binary strings (84). Each binary string includes a number of binary base pairs. The genetic sequence analyzer is further configured to generate a polynomial (EDF) based on entropy values determined for the binary strings (e.g., 50 of FIG. 5).

Figure 9:
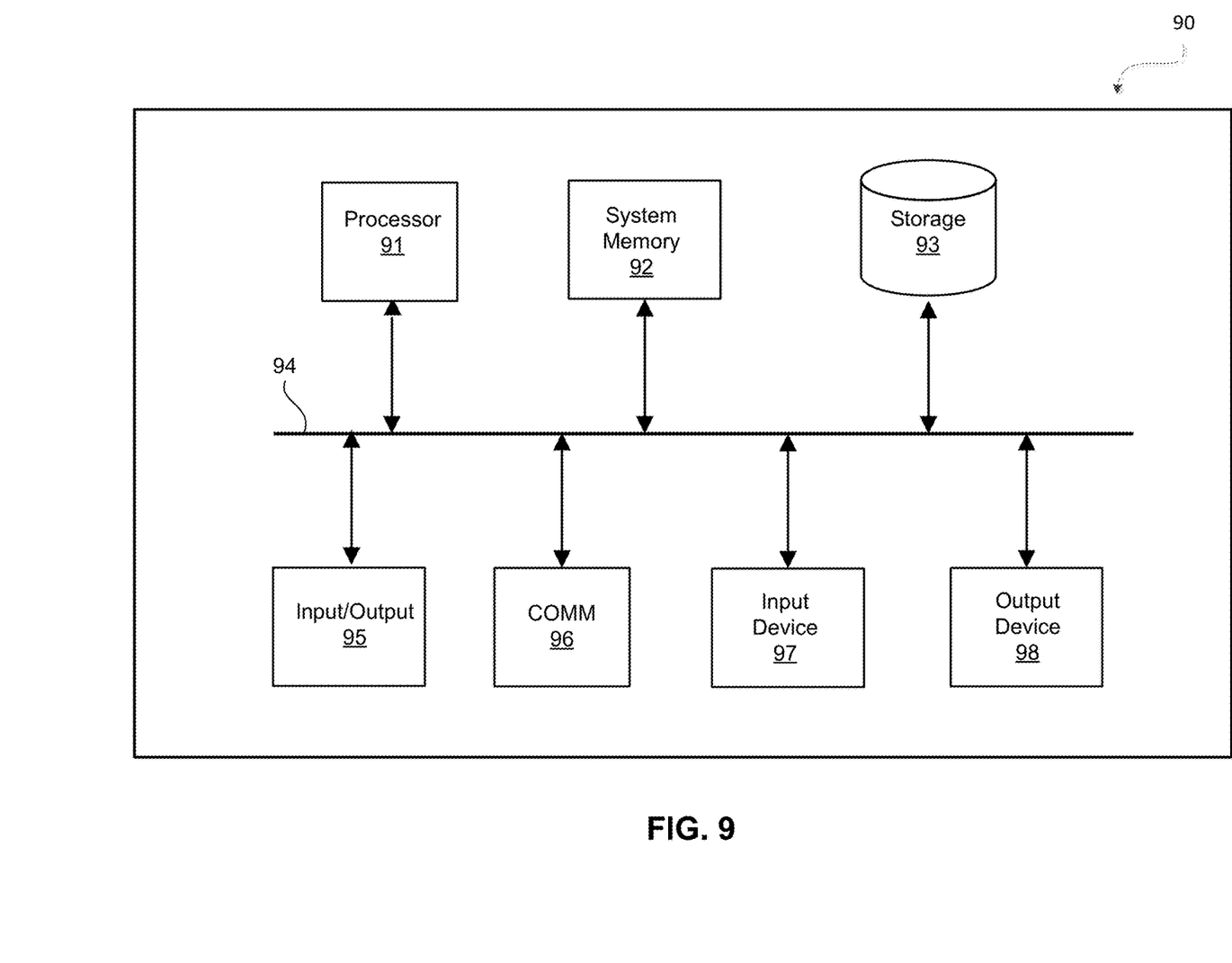
FIG. 9 is a block diagram illustrating an example computer system with which certain aspects of the subject technology can be implemented.

FIG. 9 is a block diagram illustrating an example computer system 900 with which certain aspects of the subject technology can be implemented. In some aspects, the computer system 90 may represent the server 12, the computing device 13 and/or the mobile device 14 of FIG. 1. In certain aspects, the computer system 90 may be implemented using hardware or a combination of software and hardware, either in a dedicated server or integrated into another entity or distributed across multiple entities.

Computer system 90 (e.g., server 12, the computing device 13 or the portable communication device 14) includes a bus 94 or other communication mechanism for communicating information and a processor 91 coupled with bus 94 for processing information. According to one aspect, the computer system 90 can be a cloud computing server of an infra-structure-as-a-service (IaaS) and can be able to support platform-as-a-service (PaaS) and software-as-a-service (SaaS).

Computer system 90 can include, in addition to hardware, code that creates an execution environment for the computer program in question, e.g., code that constitutes processor firmware, a protocol stack, a database management system, an operating system, or a combination of one or more of them stored in an included memory 92, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 94 for storing information and instructions to be executed by processor 91. The processor 91 and the memory 92 can be supplemented by, or incorporated in, special purpose logic circuitry.

The instructions may be stored in the memory 92 and implemented in one or more computer program products, i.e., one or more modules of computer program instructions encoded on a computer readable medium for execution by, or to control the operation of, the computer system 90, and according to any method well known to those of skill in the art. In some embodiments, the memory 92 may represent the memory 26 of FIG. 2.

A computer program as discussed herein does not necessarily correspond to a file in a file system. A program can be stored in a portion of a file that holds other programs or data (e.g., one or more scripts stored in a markup language document), in a single file dedicated to the program in question or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 90 further includes a data storage device 93 such as a magnetic disk or optical disk, coupled to bus 94 for storing information and instructions. Computer system 90 may be coupled via input/output module 95 to various devices. The input/output module 95 can be any input/output module. Example input/output modules 95 include data ports such as USB ports. In addition, input/output module 95 may be provided in communication with processor 91, so as to enable near area communication of computer system 90 with other devices. The input/output module 95 may provide, for example, for wired communication in some implementations or for wireless communication in other implementations, and multiple interfaces may also be used. The input/output module 95 is configured to connect to a communications module 96. Example communications modules 96 may include networking interface cards, such as Ethernet cards and modems.

In certain aspects, the input/output module 95 is configured to connect to a plurality of devices, such as an input device 97 and/or an output device 98. Example input devices 97 include a keyboard and a pointing device, e.g., a mouse or a trackball, by which a user can provide input to the computer system 90. Other kinds of input devices 97 can be used to provide for interaction with a user as well, such as a tactile input device, visual input device, audio input device or brain-computer interface device.

According to one aspect of the present disclosure, at least portions of the processes 30 and 40 and the method 80 can be implemented using the computer system 90 in response to processor 91 executing one or more sequences of one or more instructions contained in memory 92. Such instructions may be read into memory 92 from another machine-readable medium, such as data storage device 93. Execution of the sequences of instructions contained in main memory 92 causes processor 91 to perform the process steps described herein. One or more processors in a multi-processing arrangement may also be employed to execute the sequences of instructions contained in memory 92. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., such as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware or front end components.

In one aspect, a method may be an operation, an instruction or a function and vice versa. In one aspect, a clause or a claim may be amended to include some or all of the words (e.g., instructions, operations, functions or components) recited in other one or more clauses, one or more words, one or more sentences, one or more phrases, one or more paragraphs and/or one or more claims.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items and/or at least one of each of the items. By way of example, the phrases "at least one of A, B, and C" or "at least one of A, B, or C" each refer to only A, only B, or only C; any combination of A, B, and C; and/or at least one of each of A, B, and C.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for".

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A system for computationally analyzing genetic base pairs, the system comprising:
   a memory; and
   a processor coupled to the memory and configured to:
      receive a plurality of genetic sequences from a genetic sequencer device;
      generate, for each genetic sequence of the plurality of genetic sequences, a binary sequence;
      partition each binary sequence into a set of binary strings, each binary string of the set of binary strings including multiple binary base pairs;
      determine a set of entropy values, each entropy value of the set of entropy values being associated with a binary string of the set of binary strings; and
      generate an entropy distribution function (EDF) based on the set of entropy values;
      wherein each genetic sequence of the plurality of genetic sequences corresponds to a genetic sample, and wherein the EDF corresponds to a first genetic sample; and
      wherein the processor is further configured to compare the EDF with EDFs corresponding to multiple genetic samples to identify substantially overlapping areas.

2. The system of claim 1, wherein the EDF comprises a polynomial function, wherein the processor is further configured to determine exponents of terms of the polynomial function based on the set of entropy values.

3. The system of claim 2, wherein the processor is further configured to determine coefficients of the terms of the polynomial function based on an average count of the multiple binary base pairs.

4. The system of claim 1, wherein the processor is further configured to identify one or more local maxima in the EDF.

5. The system of claim 4, wherein the processor is further configured to identify one or more other local maxima in the identified substantially overlapping areas of the EDFs corresponding to the multiple genetic samples.

6. The system of claim 5, wherein the processor is further configured to determine a set of distances between at least one of the one or more local maxima in the EDF and one of the one or more other local maxima that best correlates the at least one of the one or more local maxima in the EDF.

7. The system of claim 6, wherein the processor is further configured to rank distance values of the set of distances to determine proximity between variants of each genetic sequence of the plurality of genetic sequences.

8. The system of claim 7, wherein the processor is further configured to identify genetic sequences with lowest deviations based on the ranked distance values.

9. The system of claim 8, wherein the processor is further configured to determine a count of mutations between the genetic sequences of the plurality of genetic sequences.

10. The system of claim 8, wherein the processor is further configured to identify areas of each genetic sequence of the plurality of genetic sequences that are more susceptible to producing stable changes.

11. The system of claim 1, wherein the processor is further configured to partition each binary sequence into the set of binary strings that are equal in length.

12. The system of claim 1, wherein the processor is further configured to partition each binary sequence into the set of binary strings that include at least one common repeating sequence of binary pairs.

13. A system comprising:
a genetic sequencer device configured to generate multiple genetic sequences associated with multiple genetic samples;
a processor configured to generate, for each genetic sequence of the multiple genetic sequences, a binary sequence; and
a genetic sequence analyzer configured to analyze the multiple genetic sequences
by:
partitioning each binary sequence into multiple binary strings, each binary string of the multiple binary strings including a plurality of binary pairs; and
generating an entropy distribution function (EDF) based on entropy values determined for binary strings of the multiple binary strings; and
wherein the genetic sequence analyzer is configured to determine exponents of terms of the polynomial EDF based on the entropy values, and to determine coefficients of the terms of the polynomial EDF based on an average count of the multiple binary strings.

14. The system of claim 13, wherein the genetic sequence analyzer is further configured to generate multiple polynomial EDFs, each polynomial EDF of the multiple polynomial EDFs corresponding to a genetic sample of the multiple genetic samples.

15. The system of claim 14, wherein the genetic sequence analyzer is further configured to identify substantially matched sections of two or more polynomial EDFs of the multiple polynomial EDFs, wherein sections of the two or more polynomial EDFs are selected for comparison by using a variable-width search window, and wherein a width of the variable-width search window is changed in a number of iterations.

16. The system of claim 15, wherein the genetic sequence analyzer is further configured to determine scores associated with identified substantially matched sections, and to rank the scores to determine best matching genetic samples of the multiple genetic samples.

17. A method of computationally analyzing genetic base pairs, comprising:
configuring a processor to:
receive a plurality of genetic sequences from a genetic sequencer device; and
to generate, for each genetic sequence of the plurality of genetic sequences, a binary sequence; and
configuring a genetic sequence analyzer to:
partition the binary sequence into multiple binary strings, each binary string of the multiple binary strings including a plurality of binary base pairs; and
generate a polynomial entropy distribution function (EDF) based on entropy values determined for binary strings of the multiple binary strings.

* * * * *

SEQUENCE LISTING

<160> NUMBER OF SEQ ID NOS: 2

<210> SEQ ID NO 1
<211> LENGTH: 100
<212> TYPE: DNA
<213> ORGANISM: Artificial Sequence
<220> FEATURE:
<223> OTHER INFORMATION: Synthetic

<400> SEQUENCE: 1
gtacatagat gatagatata gatacgatag ccagatgacg tgatagataa gcatgctagt      60
agtgcagata gataatgaat actagacttg gaactagatc                           100

<210> SEQ ID NO 2
<211> LENGTH: 100
<212> TYPE: DNA
<213> ORGANISM: Artificial Sequence
<220> FEATURE:
<223> OTHER INFORMATION: Synthetic

<400> SEQUENCE: 2
gtacatagat gatagatata gatacgatag ccagatgacg tgatagataa gcatgctagt      60
agtgcagata gataatgaat actagacttg gaactagatc                           100